(12) United States Patent
Nakazato et al.

(10) Patent No.: US 7,365,078 B2
(45) Date of Patent: Apr. 29, 2008

(54) TRIAZA-CYCLOPENTA[CD]INDENE DERIVATIVES

(75) Inventors: Atsuro Nakazato, Tokyo (JP); Taketoshi Okubo, Tokyo (JP); Dai Nozawa, Tokyo (JP); Tomoko Tamita, Tokyo (JP); Ludo E. J. Kennis, Beerse (BE)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/584,952

(22) PCT Filed: Jan. 6, 2005

(86) PCT No.: PCT/JP2005/000323

§ 371 (c)(1),
(2), (4) Date: Sep. 13, 2006

(87) PCT Pub. No.: WO2005/066178

PCT Pub. Date: Jul. 21, 2005

(65) Prior Publication Data

US 2007/0060602 A1    Mar. 15, 2007

(30) Foreign Application Priority Data

Jan. 6, 2004   (JP)   .............................. 2004-001312

(51) Int. Cl.
  *A01N 43/54*   (2006.01)
  *A61K 31/505*  (2006.01)
  *C07D 239/00*  (2006.01)
  *C07D 471/00*  (2006.01)
  *C07D 487/00*  (2006.01)
  *C07D 491/00*  (2006.01)

(52) U.S. Cl. ...................................... 514/267; 544/250
(58) Field of Classification Search .................... None
See application file for complete search history.

(56) References Cited

U.S. PATENT DOCUMENTS

| 6,187,781 B1 | 2/2001 | Nakazato et al. |
| 6,600,038 B1 | 7/2003 | Nakazato et al. |
| 6,853,732 B2 | 2/2005 | Nakazato et al. |
| 2005/0209253 A1 | 9/2005 | Nakazato et al. |

FOREIGN PATENT DOCUMENTS

| WO | 98/42699 A1 | 1/1998 |
| WO | 2006/001511 A1 | 1/1998 |
| WO | 00/53604 A1 | 9/2000 |
| WO | WO 01/83486 A1 | 11/2001 |
| WO | WO 01/87889 A1 | 11/2001 |
| WO | 02/02549 A1 | 1/2002 |
| WO | WO 02/094826 A1 | 11/2002 |
| WO | 2004/058767 A1 | 7/2004 |
| WO | 2005/066142 A3 | 7/2005 |
| WO | 2005/066178 A1 | 7/2005 |
| WO | 2005/066182 A1 | 7/2005 |
| WO | 2005/085253 A1 | 9/2005 |
| WO | 2006/001501 A1 | 1/2006 |

OTHER PUBLICATIONS

Bonamico, et al., Condensation Reactions of Tetracyanoethylene and its Monoanion Promoted by Lewis Acids: Synthesis and Crystal, Molecular, and Electronic Structure of a Novel Heterocycle, the 2, 3, 6, 7-Tetracyano-5-(tricyanoethenylimino)-3H-1,4,7b-triazabenzo[i,,j]pentalenide Ion, J. Chem. Soc. Perkin Trans. 2, 121-125 (1990).*

* cited by examiner

*Primary Examiner*—James O. Wilson
*Assistant Examiner*—Erich Leeser
(74) *Attorney, Agent, or Firm*—Sughrue Mion, PLLC

(57) ABSTRACT

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, dermatitides, schizophrenia, pain, etc. A triaza-cyclopenta[cd]indene derivative represented by the following formula [I]: has a high affinity for CRF receptors and is effective against diseases in which CRF is considered to be involved 5 Claims, No Drawings

US 7,365,078 B2

TRIAZA-CYCLOPENTA[CD]INDENE DERIVATIVES

This Application is a 371 of PCT/JP2005/000323, filed Jan. 6, 2005; the disclosure of which is incorporated herein by reference.

DETAILED DESCRIPTION OF THE INVENTION

1. Technical Field

The present invention relates to a therapeutic agent for diseases in which corticotropin releasing factor (CRF) is considered to be involved, such as depression, anxiety, Alzheimer's disease, Parkinson's disease, Huntington's chorea, eating disorder, hypertension, gastral diseases, drug dependence, cerebral infarction, cerebral ischemia, cerebral edema, cephalic external wound, inflammation, immunity-related diseases, alpecia, irritable bowel syndrome, sleep disorders, epilepsy, dermatitides, schizophrenia, pain, etc.

2. Description of the Prior Art

CRF is a hormone comprising 41 amino acids (Science, 213, 1394-1397, 1981; and J. Neurosci., 7, 88-100, 1987), and it is suggested that CRF plays a core role in biological reactions against stresses (Cell. Mol. Neurobiol., 14, 579-588, 1994; Endocrinol., 132, 723-728, 1994; and Neuroendocrinol. 61, 445-452, 1995). For CRF, there are the following two paths: a path by which CRF acts on peripheral immune system or sympathetic nervous system through hypothalamus-pituitary-adrenal system, and a path by which CRF functions as a neurotransmitter in central nervous system (in Corticotropin Releasing Factor: Basic and Clinical Studies of a Neuropeptide, pp. 29-52, 1990). Intraventricular administration of CRF to hypophy-sectomized rats and normal rats causes an anxiety-like symptom in both types of rats (Pharmacol. Rev., 43, 425-473, 1991; and Brain Res. Rev., 15, 71-100, 1990). That is, there are suggested the participation of CRF in hypothalamus-pituitary-adrenal system and the pathway by which CRF functions as a neurotransmitter in central nervous system.

The review by Owens and Nemeroff in 1991 summarizes diseases in which CRF is involved (Pharmacol. Rev., 43, 425-474, 1991). That is, CRF is involved in depression, anxiety, Alzheimer's disease, Parkinson's disease, Huntington's chorea, eating disorder, hypertension, gastrointestinal diseases, drug dependence, inflammation, immunity-related diseases, etc. It has recently been reported that CRF is involved also in epilepsy, cerebral infarction, cerebral ischemia, cerebral edema, and cephalic external wound (Brain Res. 545, 339-342, 1991; Ann. Neurol. 31, 48-498, 1992; Dev. Brain Res. 91, 245-251, 1996; and Brain Res. 744, 166-170, 1997). Accordingly, antagonists against CRF receptors are useful as therapeutic agents for the diseases described above.

PROBLEM(S) TO BE SOLVED BY INVENTION

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, epilepsy, dermatitides, schizophrenia, pain, etc.

MEANS FOR SOLVING PROBLEM

The present inventors earnestly investigated triaza-cyclopenta[cd]indene derivatives that have a high affinity for CRF receptors, whereby the present invention has been accomplished.

The present invention is triaza-cyclopenta[cd]indene derivatives explained below.

A triaza-cyclopenta[cd]indene derivative represented by the following formula [I]:

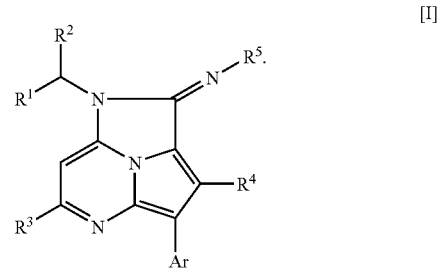

(wherein $R^1$ and $R^2$ are the same or different, and independently are hydrogen, $C_{1-6}$alkyl, $C_{3-7}$cycloalkyl, $C_{3-7}$cycloalkyl-$C_{1-6}$alkyl, $C_{1-6}$alkoxy-$C_{1-6}$alkyl, hydroxy-$C_{1-6}$alkyl, cyano-$C_{1-6}$alkyl, carbamoyl-$C_{1-6}$alkyl or di($C_{1-6}$alkyl)amino-$C_{1-6}$alkyl, cyano, carbamoyl or aryl;

$R^3$ is hydrogen, $C_{1-6}$alkyl, $C_{3-7}$cycloalkyl, $C_{3-7}$cycloalkyl-$C_{1-6}$alkyl, halogen, $C_{1-6}$alkoxy, $C_{3-7}$cycloalkyloxy, $C_{1-6}$alkylthio or —N($R^6$)$R^7$;

$R^4$ is hydrogen, $C_{1-6}$alkyl, $C_{3-7}$cycloalkyl or $C_{3-7}$cycloalkyl-$C_{1-6}$alkyl;

$R^5$ is hydrogen, $C_{1-6}$alkyl, aryl-$C_{1-6}$alkyl or carbamoyl;

Ar is aryl or heteroaryl which aryl or heteroaryl is unsubstituted or substituted with 1 or more substituents, which are the same or different, selected from the group consisting of halogen, $C_{1-6}$alkyl, $C_{3-7}$cycloalkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, cyano, nitro, hydroxy, —$CO_2R^8$, —C(=O)$R^9$, —CONR$^{10}$R$^{11}$, —OC(=O)R$^{12}$, —NR$^{13}$CO$_2$R$^{14}$, —S(=O)$_r$NR$^{15}$R$^6$, trifluoromethyl, trifluoromethoxy, difluoromethoxy, fluoromethoxy and —N(R$^{17}$)R$^{18}$;

$R^8$ and $R^{14}$ are the same or different, and independently are hydrogen or $C_{1-5}$alkyl, $C_{3-8}$cycloalkyl, $C_{3-8}$cycloalkyl-$C_{1-5}$alkyl, aryl or aryl-$C_{1-5}$alkyl;

$R^6$, $R^7$, $R^9$, $R^{10}$, $R^{11}$, $R^{12}$, $R^{13}$, $R^{15}$, $R^{16}$, $R^{17}$ and $R^{18}$ are the same or different, and independently are hydrogen, $C_{1-6}$alkyl or $C_{3-7}$cycloalkyl;

r is 1 or 2) or individual isomers thereof or racemic or non-racemic mixtures of isomers thereof, or pharmaceutically acceptable salts and hydrates thereof.

The terms used in the present specification have the following meanings.

The term "$C_{1-6}$alkyl" means a straight chain or branched chain alkyl group of 1 to 6 carbon atoms, such as methyl, ethyl, propyl, isopropyl, butyl, isobutyl, tert-butyl, sec-butyl, pentyl, isopentyl, hexyl, isohexyl or the like.

The term "$C_{3-7}$cycloalkyl" means a cyclic alkyl group of 3 to 7 carbon atoms, such as cyclopropyl, cyclobutyl, cyclopentyl, cyclohexyl, cycloheptyl or the like.

The term "$C_{3-7}$cycloalkyl-$C_{1-6}$alkyl" means a substituted $C_{1-6}$alkyl group having the above-mentioned $C_{3-7}$cycloalkyl as the substituent, such as cyclopropylmethyl, 2-cyclopropylethyl, 2-cyclopentylethyl or the like.

The term "$C_{1-6}$alkoxy" means a straight chain or branched chain alkoxy group of 1 to 6 carbon atoms, such as methoxy, ethoxy, propoxy, isopropyloxy, butoxy, isobutyloxy, pentyloxy, isopentyloxy or the like.

The term "$C_{3-7}$cycloalkyloxy" means a cyclic alkoxy group of 3 to 7 carbon atoms, such as cyclopropyloxy, cyclobutyloxy, cyclopentyloxy or the like.

The term "$C_{1-6}$alkoxy-$C_{1-6}$alkyl" means a substituted $C_{1-6}$alkyl group having the above-mentioned $C_{1-6}$alkoxy group as the substituent, such as methoxymethyl, 2-methoxyethyl, 2-ethoxyethyl or the like.

The term "hydroxy-$C_{1-6}$alkyl" means a substituted $C_{1-6}$alkyl group having hydroxy group, such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl or the like.

The term "cyano-$C_{1-6}$alkyl" means a substituted $C_{1-6}$alkyl group having cyano group, such as cyanomethyl, 1-cyanoethyl, 2-cyanoethyl, 3-cyanopropyl, 4-cyanobutyl, 5-cyanopentyl or the like.

The term "carbonyl-$C_{1-6}$alkyl" means a substituted $C_{1-6}$alkyl group having a carbamoyl group, such as carbamoylmethyl, 1-carbamoylethyl, 2-carbamoylethyl, 3-carbamoylpropyl, 4-carbamoylbutyl, 5-carbamoylpentyl or the like.

The term "di($C_{1-6}$alkyl)amino" means an amino group having two above-mentioned $C_{1-6}$alkyl groups, such as dimethylamino, diethylamino, dipropylamino or the like.

The term "di($C_{1-6}$alkyl)amino-$C_{1-6}$alkyl" means a substituted $C_{1-6}$alkyl group having the above-mentioned di($C_{1-6}$alkyl)amino group, such as 2-dimethylaminoethyl, 3-dimethylaminopropyl or the like.

The term "aryl" means a monocyclic or bicyclic group of 6 to 12 ring carbon atoms having at least one aromatic ring, such as phenyl, naphthyl, or the like.

The term "aryl-$C_{1-6}$alkyl" means a substituted $C_{1-6}$alkyl group having an above-mentioned aryl group, such as benzyl, phenethyl or the like.

The term "heteroaryl" means a monocyclic or bicyclic group of 5 to 12 ring atoms having at least one aromatic ring having in its ring 1 to 4 atoms which may be the same or different and are selected from nitrogen, oxygen and sulfur, such as pyridyl, pyrimidinyl, imidazolyl, quinolyl, indolyl, benzofuranyl, quinoxalinyl, benzo[1,2,5]thiadiazolyl, benzo[1,2,5]oxadiazolyl or the like.

The term "halogen" means fluorine, chlorine, bromine or iodine atom.

The term "$C_{2-6}$alkenyl" means a straight chain or branched chain alkenyl group of 2 to 6 carbon atoms, such as vinyl, isopropenyl, allyl or the like.

The term "$C_{2-6}$alkynyl" means a straight chain or branched chain alkynyl group of 2 to 6 carbon atoms, such as ethynyl, prop-1-ynyl, prop-2-ynyl or the like.

The term "$C_{1-6}$alkylthio" means a straight chain or branched chain alkylthio group of 1 to 6 carbon atoms, such as methylthio, ethylthio, propylthio or the like.

The term "$C_{1-6}$alkylsulfinyl" means a straight chain or branched chain alkylsulfinyl group of 1 to 6 carbon atoms, such as methylsulfinyl, ethylsulfinyl, propylsulfinyl or the like.

The term "$C_{1-6}$alkylsulfonyl" means a straight chain or branched chain alkylsulfonyl group of 1 to 6 carbon atoms, such as methylsulfonyl, ethylsulfonyl, propylsulfonyl or the like.

The phrase "aryl or heteroaryl which aryl or heteroaryl is unsubstituted or substituted with 1 or more substituents, which are the same or different, selected from the group consisting of halogen, $C_{1-6}$alkyl, $C_{3-7}$cycloalkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, cyano, nitro, hydroxy, —$CO_2R^8$, —$C(=O)R^9$, —$CONR^{10}R^{11}$, —$OC(=O)R^{12}$, —$NR^{13}CO_2R^{14}$, —$S(=O)_rNR^{15}R^{16}$, trifluoromethyl, trifluoromethoxy, difluoromethoxy, fluoromethoxy and —$N(R^{17})R^{18}$" includes, for example, 2,4-dimethylphenyl, 2,6-dimethylphenyl, 2,4-dibromophenyl, 2-bromo-4-isoproylphenyl, 2,4-dichlorophenyl, 2,6-dichlorophenyl, 2-chloro-4-trifluoromethylphenyl, 4-methoxy-2-methylphenyl, 2-chloro-4-trifluoromethoxyphenyl, 4-isopropyl-2-methylthiophenyl, 2,4,6-trimethylphenyl, 4-bromo-2,6-dimethylphenyl, 4-bromo-2,6-diethylphenyl, 4-chloro-2,6-dimethylphenyl, 2,4,6-tribromophenyl, 2,4,5-tribromophenyl, 2,4,6-trichlorophenyl, 2,4,5-trichlorophenyl, 4-bromo-2,6-dichlorophenyl, 6-chloro-2,4-dibromophenyl, 2,4-dibromo-6-fluorophenyl, 2,4-dibromo-6-methylphenyl, 2,4-dibromo-6-methoxyphenyl, 2,4-dibromo-6-methylthiophenyl, 2,6-dibromo-4-isopropylphenyl, 2,6-dibromo-4-trifluoromethylphenyl, 2-bromo-4-trifluoromethylphenyl, 4-bromo-2-chlorophenyl, 2-bromo-4-chlorophenyl, 4-bromo-2-methylphenyl, 4-chloro-2-methylphenyl, 2,4-dimethoxyphenyl, 2,6-dimethyl-4-methoxyphenyl, 4-chloro-2,6-dibromophenyl, 4-bromo-2,6-difluorophenyl, 2,6-dichloro-4-trifluoromethylphenyl, 2,6-dichloro-4-trifluoromethoxyphenyl, 2,6-dibromo-4-trifluoromethoxyphenyl, 2-chloro-4,6-dimethylphenyl, 2-bromo-4,6-dimethoxyphenyl, 2-bromo-4-isopropyl-6-methoxyphenyl, 2,4-dimethoxy-6-methlphenyl, 6-dimethylamino-4-methylpyridin-3-yl, 2-chloro-6-trifluoromethylpyridin-3-yl, 2-chloro-6-trifluoromethoxypyridin-3-yl, 2-chloro-6-methoxypyridin-3-yl, 6-methoxy-2-trifluoromethylpyridin-3-yl, 2-chloro-6-difluoromethylpyridin-3-yl, 6-methoxy-2-methylpyridin-3-yl, 2,6-dimethoxypyridin-3-yl, 4,6-dimethyl-2-trifluoromethylpyrimidin-5-yl, 2-dimethylamino-6-methylpyridin-3-yl.

The "pharmaceutically acceptable salts" in the present invention include, for example, salts with an inorganic acid such as sulfuric acid, hydrochloric acid, hydrobromic acid, phosphoric acid, nitric acid or the like; salts with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like; salts with one or more metal ions such as lithium ion, sodium ion, potassium ion, calcium ion, magnesium ion, zinc ion, aluminium ion or the like; salts with amines such as ammonia, arginine, lysine, piperazine, choline, diethylamine, 4-phenylcyclohexylamine, 2-aminoethanol, benzathine or the like.

In a compound of the present invention, isomers such as diastereomers, enantiomers, geometricisomers and tautomeric forms may exist. The compound of the present invention includes any individual isomers and the racemic and non-racemic mixtures of the isomers.

Preferable examples of the compound of the present invention are as follows.

That is preferable are compounds represented by the formula [I], wherein $R^3$ is $C_{1-6}$alkyl; $R^4$ is hydrogen or $C_{1-6}$alkyl; $R^5$ is hydrogen or $C_{1-6}$alkyl; Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N($R^7$)$R^{18}$ (wherein $R^{17}$ and $R^{18}$ are the same or different, and independently are hydrogen or $C_{1-3}$alkyl). More preferable are compounds of formula [I], wherein $R^3$ is $C_{1-3}$alkyl; $R^4$ is hydrogen or $C_{1-6}$alkyl; $R^5$ is hydrogen or $C_{1-3}$alkyl; Ar is phenyl which phenyl is substituted with two or three substituents, which are the same or different, selected from the group consisting of halogen or $C_{1-3}$alkyl.

The compound of the formula [I] can be produced, for example, by the process shown in the following reaction scheme 1 (in the following reaction scheme, $R^1$, $R^2$, $R^3$, $R^4$ and Ar are as defined above, LG is chloro, bromo, iodo, methanesulfonyloxy, benzenesulfonyloxy, toluenesulfonyloxy, trifluoromethanesulfonyloxy group, $R^a$—S(O)— or $R^a$—S(O)$_2$—, wherein $R^a$ is $C_{1-6}$alkyl or benzyl).

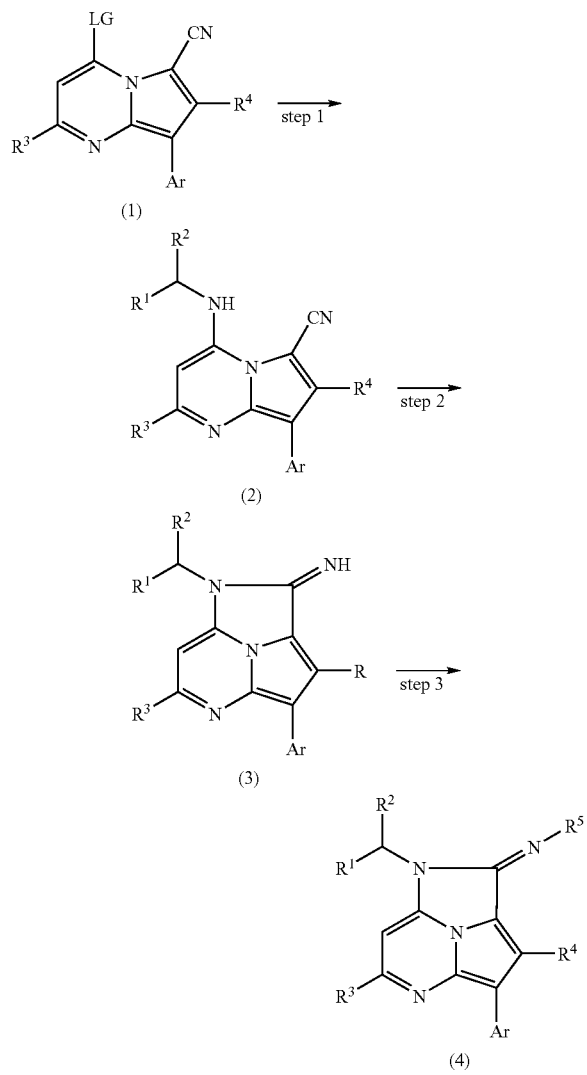

Step 1:

Compound (2) can be obtained by reacting Compound (1) with the corresponding amine in an inert solvent in the presence or absence of a base. Herein, the base includes, for example, amines such as triethylamine, N,N-diisopropylethylamine, pyridine and the like; inorganic bases such as sodium carbonate, potassium carbonate, sodium hydrogencarbonate, potassium hydrogencarbonate, potassium hydroxide, sodium hydroxide, lithium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

Step 2:

Conversion of Compound (2) into Compound (3) can be achieved in the presence of an acid in an inert solvent. Herein, the acid is an inorganic acid such as sulfuric acid, hydrochloric acid, hydrobromic acid, phosphoric acid, nitric acid or the like; an organic acid such as acetic acid, benzenesulfonic acid, methanesulfonic acid, p-toluenesulfonic acid, benzoic acid, camphorsulfonic acid, trifluoroacetic acid, trifluoromethanesulfonic acid or the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

Step 3:

Conversion of Compound (3) into Compound (4) can be achieved by using an alkylating reagent in the presence or absence of a base in an inert solvent (when $R^5$ is $C_{1-6}$alkyl) or reacting with a carbonylating reagent in the presence or absence of a base in an inert solvent and then treatment of ammonia (when $R^5$ is carbamoyl). Herein, the alkylating reagent includes conventional alkylating reagents such as iodomethane, iodoethane, bromomethane, bromoethane, dimethylsulfate, diethylsulfate or the like. The carbonylating reagent includes conventional carbonylating reagents such as phosgene, diphosgene, triphosgene, 1,1'-carbonyldiimidazole or the like. The base includes, for example, amines such as triethylamine, N,N-diisopropylethylamine, pyridine and the like; inorganic bases such as sodium carbonate, potassium carbonate, sodium hydrogencarbonate, potassium hydrogencarbonate, potassium hydroxide, sodium hydroxide, lithium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene, xylene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

The compound of the present invention can be converted to a salt with an inorganic acid such as sulfuric acid, hydrochloric acid, hydrobromic acid, phosphoric acid, nitric acid or the like; with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, naphthalene-2-sulfonic acid or the like; with an inorganic base such as lithium hydroxide, sodium hydroxide, potassium hydroxide, calcium hydroxide, magnesium hydroxide, zinc hydroxide, aluminium hydroxide or the like; or with an organic base such as ammonia, arginine, lysine, piperazine, choline, diethylamine, 4-phenylcyclohexylamine, 2-aminoethanol, benzathine or the like in an inert solvent.

The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; esters such as ethyl acetate, ethyl formate and the like; ketones such as acetone, methylethylketone and the like; hydrocarbons such as benzene, toluene and the like; amides such as N,N-dimethylformamide, N-methylpyrrolidone, N,N-dimethylacetamide and the like; acetonitrile; dichloromethane; chloroform; dimethyl sulfoxide; pyridine; water; and mixtures of solvents selected from these inert solvents.

The compound of the present invention is useful as a therapeutic or prophylactic agent for diseases in which CRF is considered to be involved. For this purpose, the compound of the present invention can be formulated into tablets, pills, capsules, granules, powders, solutions, emulsions, suspensions, injections and the like by a conventional preparation technique by adding conventional fillers, binders, disintegrators, pH-adjusting agents, solvents, etc.

The compound of the present invention can be administered to an adult patient in a dose of 0.1 to 500 mg per day in one portion or several portions orally or parenterally. The dose can be properly increased or decreased depending on the kind of a disease and the age, body weight and symptom of a patient.

EMBODIMENTS OF THE INVENTION

The present invention is concretely explained with reference to the following examples and test example, but is not limited thereto.

EXAMPLE 1

Synthesis of [4-(2-bromo-4 isopropyl-phenyl)-6-methyl-1-(1-propyl-butyl)-1H-1,5,7b-triaza-cyclopenta[cd]inden-2-ylidene]-methyl-amine hydrochloride (compound 1-010)

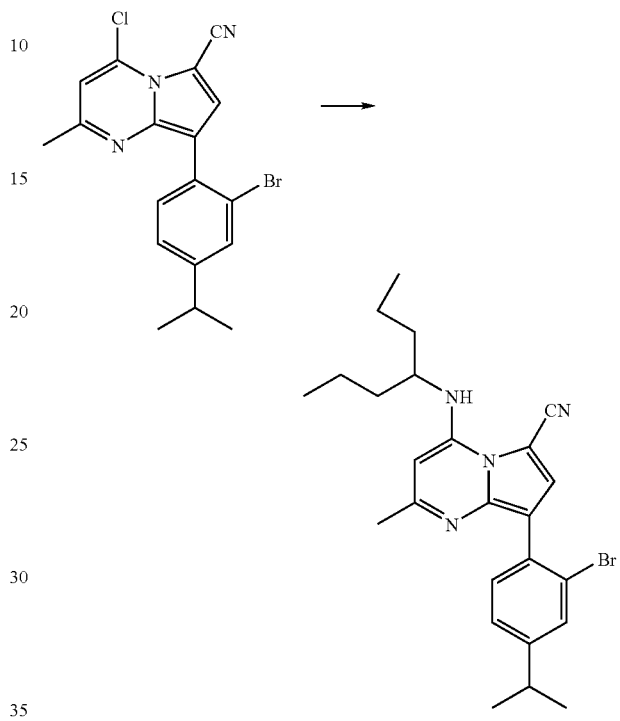

(1) A mixture of 8-(2-bromo-4-isopropyl-phenyl)-4-chloro-2-methyl-pyrrolo[1,2-a]pyrimidine-6-carbonitrile (300 mg), 1-propyl-butylamine (267 mg), N,N-diisopropylethylamine (300 mg) in ethanol (1.0 mL) was heated at reflux overnight. The reaction mixture was cooled to room temperature, poured into a saturated aqueous sodium hydrogencarbonate, and then extracted with chloroform. The organic layer was dried over anhydrous sodium sulfate and filtered. The filtrate was concentrated under reduced pressure and purified by a silica gel column chromatography (silica gel: Wako Gel (C200), eluent: hexane/ethyl acetate=20:1) to give 8-(2-bromo-4-isopropyl-phenyl)-2-methyl-4-(1-propyl-butylamino)-pyrrolo[1,2-a]pyrimidine-6-carbonitrile (321 mg) as a pale brown solid.

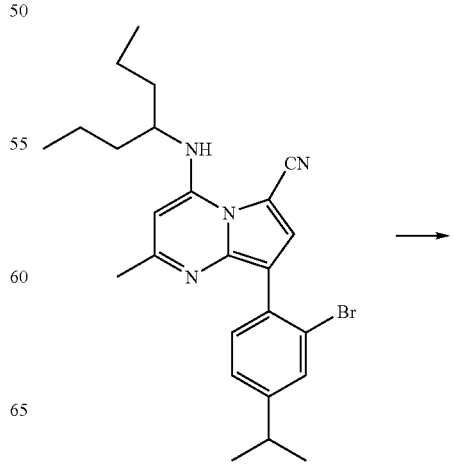

-continued

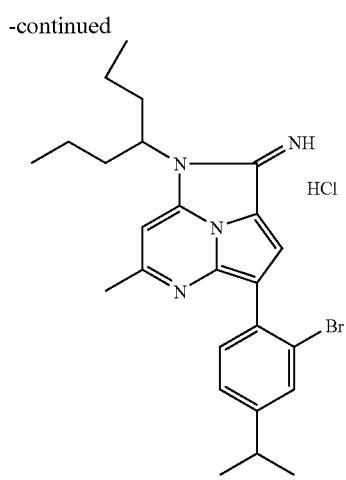

(2) To a suspension of 8-(2-bromo-4-isopropyl-phenyl)-2-methyl-4-(1-propyl-butylamino)-pyrrolo[1,2-a]pyrimidine-6-carbonitrile (321 mg) in ethanol (1.5 mL) was added conc. HCl (0.75 mL) and heated for 50° C. for 3 hours. The reaction mixture was cooled to room temperature, poured into a saturated aqueous sodium hydrogencarbonate and extracted with ethyl acetate. The organic layer was dried over anhydrous sodium sulfate and filtered. The filtrate was concentrated under reduced pressure to give crude product. To a solution of the crude product in ethyl acetate (2 mL) and ethanol (0.2 mL) was added 4M HCl/ethyl acetate (0.25 mL) under ice-cooling and concentrated under reduced pressure. The residue was crystallized from ethyl acetate to provide 4-(2-bromo-4-isopropyl-phenyl)-6-methyl-1-(1-propyl-butyl)-1H-1,5,7b-triaza-cyclopenta[cd]inden-2-ylideneamine hydrochloride (350 mg) as a solid.

(3) To a mixture of 4-(2-bromo-4-isopropyl-phenyl)-6-methyl-1-(1-propyl-butyl)-1H-1,5,7b-triaza-cyclopenta[cd]inden-2-ylideneamine hydrochloride (350 mg) and dimethylsulfate (866 mg) in tetrahydrofuran (3.5 mL) was added NaH (60% in oil, 139 mg) and heated at 65° C. for 1 hour. After addition of water, the reaction mixture was poured into 2.5 M NaOH aqueous solution, extracted with ethyl acetate. The organic layer was washed with brine and dried over anhydrous sodium sulfate and filtered. The filtrate was concentrated under reduced pressure and the residue was purified by a silica gel column chromatography (silica gel: Wako Gel (C200), eluent: chloroform/ethyl acetate=10:1) to give [4-(2-bromo-4-isopropyl-phenyl)-6-methyl-1-(1-propyl-butyl)-1H-1,5,7b-triaza-cyclopenta[cd]inden-2-ylidene]-methyl-amine (135 mg)

(4) To a suspension of [4-(2-bromo-4-isopropyl-phenyl)-6-methyl-1-(1-propyl-butyl)-1H-1,5,7b-triaza-cyclopenta[cd]inden-2-ylidene]-methyl-amine (135 mg) in a mixture of ethyl acetate (1.5 mL) and ethanol (0.2 mL) was added 4M HCl/ethyl acetate (0.25 mL) and concentrated under reduced pressure. The residue was solidified from Et$_2$O to provide the title compound as an amorphous (73 mg).

Table 1 lists the compound obtained in Example 1 and compounds obtained by the similar procedure as described in Example 1.

EXAMPLE 2

Synthesis of [4-(4-bromo-2,6-dimethyl-phenyl)-6-methyl-1-(1-propyl-butyl)-1H-1,5,7b-triaza-cyclopenta[cd]inden-2-ylidene]-urea (compound 1-013)

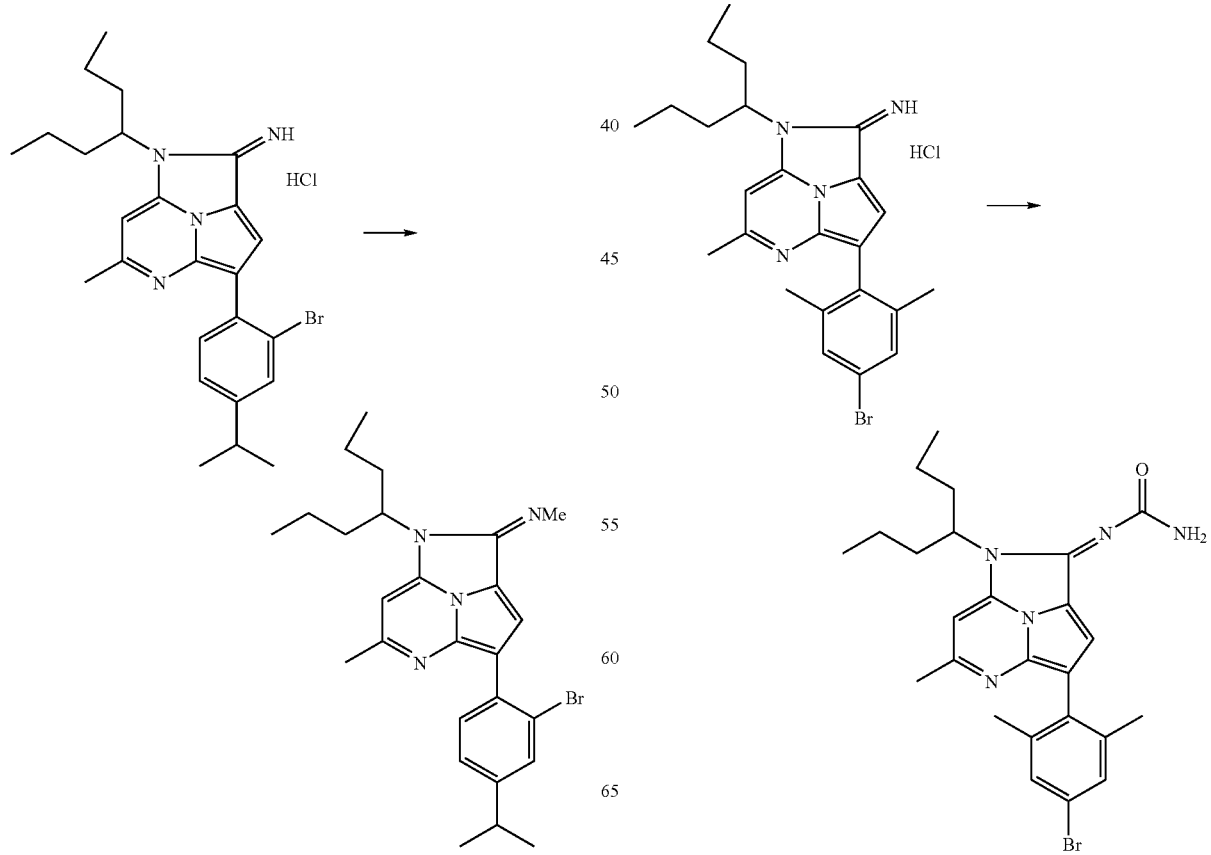

To a solution of triphosgene (1.82 g) in chloroform (9 mL) was added dropwise a solution of 4-(4-bromo-2,6-dimethylphenyl)-6-methyl-1-(1-propyl-butyl)-1H-1,5,7b-triaza-cyclopenta[cd]inden-2-ylideneamine hydrochloride (300 mg) synthesized by the same procedure as in example 1 and N,N-diisopropylethylamine (174 mg) in chloroform (3 mL) in an ice-cooling bath and stirred at room temperature for 1 hour. The reaction mixture was added dropwise into 25% an aqueous $NH_3$ solution (10 mL) in an ice-cooling bath and stirred at room temperature for 2 hours. The reaction mixture was poured into $H_2O$ and extracted with chloroform. The organic layer was washed with brine, dried over anhydrous sodium sulfate and filtered. The filtrate was concentrated under reduced pressure and the residue was purified by a silica gel column chromatography (silica gel: Wako Gel (C200), eluent: hexane/ethyl acetate=1:1) to give a solid. The solid was washed with diisopropylether and the title compound (42 mg) was obtained.

TABLE 1[*1]

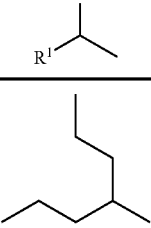

| Com. No. | Ex. No. | $R^1$ / $R^2$ | $R^3$ | $R^4$ | $R^5$ | Ar | melting point (° C.) (solvent for crystallization) |
|---|---|---|---|---|---|---|---|
| 1-001 | 1 | 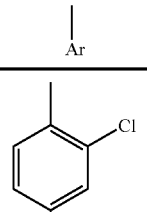 | $CH_3$ | H | H | 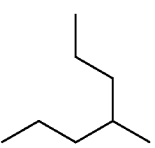 | 202-204[*2] (EtOAc/IPE) |
| 1-002 | 1 | 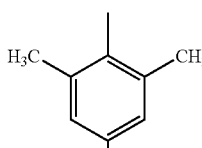 | $CH_3$ | H | H | 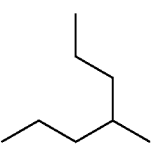 | 204-206[*2] (EtOAc/IPE) |
| 1-003 | 1 | 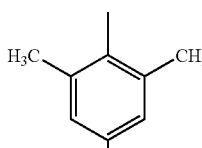 | $CH_3$ | H | H | 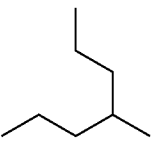 | 206-208[*2] (EtOAc/IPE) |
| 1-004 | 1 | 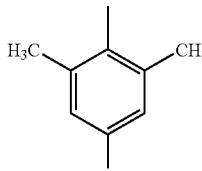 | $CH_3$ | H | H | 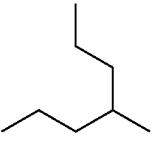 | 201-203[*2] ($H_2O$) |
| 1-005 | 1 | 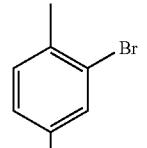 | $CH_3$ | H | H | | amorphous[*2] |

TABLE 1*[1]-continued

| Com. No. | Ex. No. | R[1] R[2] (CH group) | R[3] | R[4] | R[5] | Ar | melting point (° C.) (solvent for crystallization) |
|---|---|---|---|---|---|---|---|
| 1-006 | 1 | 4-methylheptyl | CH$_3$ | H | H | 2-Br-4-CF$_3$-phenyl | 218-220*[2] (H$_2$O) |
| 1-007 | 1 | 4-methylheptyl | CH$_3$ | H | H | 2,4-diBr-phenyl | 220-222*[2] (H$_2$O) |
| 1-008 | 1 | 4-methylheptyl | CH$_3$ | H | CH$_3$ | 2,6-diMe-4-Br-phenyl | 183-185*[3] (EtOAc) |
| 1-009 | 1 | 4-methylheptyl | CH$_3$ | H | CH$_3$ | 2,6-diMe-4-Cl-phenyl | 192-194*[3] (EtOAc) |
| 1-010 | 1 | 4-methylheptyl | CH$_3$ | H | CH$_3$ | 2-Br-4-iPr-phenyl | amorphous*[2] |
| 1-011 | 1 | 4-methylheptyl | CH$_3$ | H | CH$_3$ | 2-Br-4-CF$_3$-phenyl | amorphous*[2] |

TABLE 1*1-continued
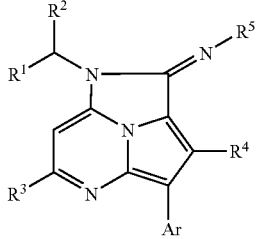
| Com. No. | Ex. No. | R1 R2 | R3 | R4 | R5 | Ar | melting point (° C.) (solvent for crystallization) |
|---|---|---|---|---|---|---|---|
| 1-012 | 1 |  | CH3 | H | CH3 | 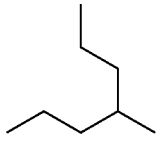 | amorphous*2 |
| 1-013 | 2 | 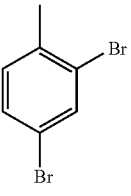 | CH3 | H | CONH2 | 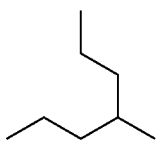 | 198-200 (IPE) |
| 1-014 | 1 | 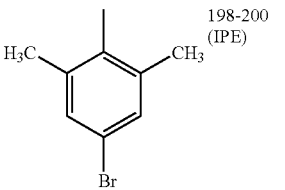 | CH3 | H | H | 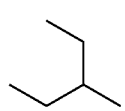 | 214-216 (H2O) |
| 1-015 | 1 | 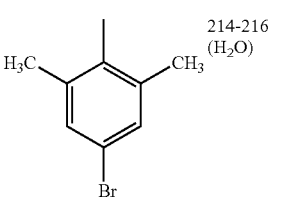 | CH3 | H | CH3 | 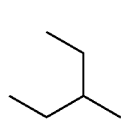 | 180-182*3 (EtOAc) |
| 1-016 | 1 | 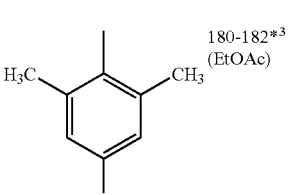 | CH3 | H | H | 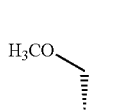 | amorphous*2 |

TABLE 1*[1]-continued
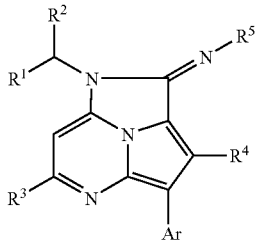
| Com. No. | Ex. No. | R[1] R[2] | R[3] | R[4] | R[5] | Ar | melting point (° C.) (solvent for crystallization) |
|---|---|---|---|---|---|---|---|
| 1-017 | 1 |  | CH₃ | H | CH₃ | 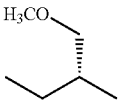 | 185-187*[3] (EtOAc) |
| 1-018 | 1 | 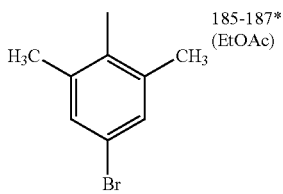 | CH₃ | H | H | 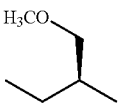 | amorphous*[2] |
| 1-019 | 1 | 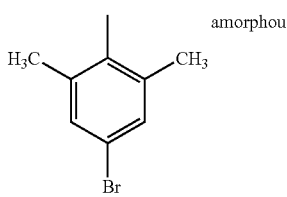 | CH₃ | H | CH₃ | 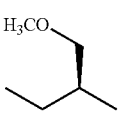 | 188-190*[3] (EtOAc) |
| 1-020 | 1 | 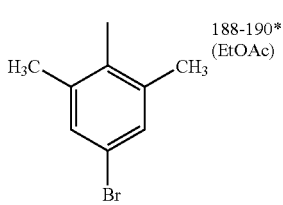 | CH₃ | H | H | 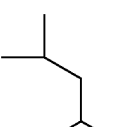 | amorphous*[2] |
| 1-021 | 1 | 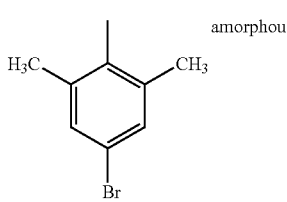 | CH₃ | H | CH₃ | 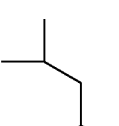 | 174-176*[3] (EtOAc) |

TABLE 1*¹-continued

| Com. No. | Ex. No. | R¹ / R² | R³ | R⁴ | R⁵ | Ar | melting point (° C.) (solvent for crystallization) |
|---|---|---|---|---|---|---|---|
| 1-022 | 1 | H₃CO— / H₃CO— (2-methylpropyl with two methoxy groups) | CH₃ | H | H | 2,6-dimethyl-4-bromophenyl | amorphous*² |

*¹Com. No. = compound number, Ex. No. = example number, solvent for crystallization; EtOAc = ethyl acetate, IPE = diisopropylether Analytical data of non-crystal compounds are described below.
1-005: MS (Pos, ES): 467 (M + 1)⁺, 469 (M + 3)⁺, 489 (M + Na)⁺, 491 (M + Na + 2)⁺; NMR (300 MHz, CDCl₃) δ 0.95 (6 H, t, J=7.3 Hz), 1.29 (6 H, t, J=7.0 Hz), 1.12-1.40 (2 H, m), 1.43-1.73 (2 H, m), 1.92-2.15 (4 H, m), 2.82-3.00 (1 H, m), 2.91 (3 H, s), 5.48 (1 H, br s), 7.10 (1 H, s), 7.22-7.30 (1 H, m), 7.55-7.63 (2 H, m), 8.57 (1 H, s), 11.10 (1 H, br s)
1-010: MS (Pos, ES): 481 (M + 1)⁺, 483 (M + 3)⁺; NMR (300 MHz, CDCl₃) δ 0.94 (6 H, t, J=7.3 Hz), 1.18-1.40 (2 H, m), 1.31 (6 H, d, J=6.8 Hz), 1.44-1.80 (2 H, m), 1.91-2.20 (4 H, m), 2.88-3.04 (1 H, m), 2.94 (3 H, s), 3.48 (3 H, d, J=4.2 Hz), 5.81 (1 H, br s), 7.17 (1 H, s), 7.34 (1 H, dd, J=1.7, 7.9 Hz), 7.63 (1 H, d, J=1.7 Hz), 7.74 (1 H, d, J=7.9 Hz), 8.04 (1 H, s), 12.5 (1 H, br s)
1-011: MS (Pos, ES): 507 (M + 1)⁺, 509 (M + 3)⁺; NMR (300 MHz, CDCl₃) δ 0.95 (6 H, t, J=7.3 Hz), 1.19-1.40 (2 H, m), 1.46-1.80 (2 H, m), 1.91-2.20 (4 H, m), 2.95 (3 H, s), 3.50 (3 H, d, J=4.7 Hz), 5.86 (1 H, br s), 7.20 (1 H, s), 7.75 (1 H, d, J=8.0 Hz), 8.02 (1 H, d, J=8.0 Hz), 8.05 (1 H, s), 8.15 (1 H, s), 12.85 (1 H, br s)
1-012: MS (Pos, ES): 517 (M + 1)⁺, 519 (M + 3)⁺, 521 (M + 5)⁺; NMR (300 MHz, CDCl₃) δ 0.94 (6 H, t, J=7.2 Hz), 1.16-1.38 (2 H, m), 1.42-1.80 (2 H, m), 1.88-2.20 (4 H, m), 2.94 (3 H, s), 3.49 (3 H, d, J=4.2 Hz), 5.83 (1 H, br s), 7.18 (1 H, s), 7.62 (1 H, dd, J=1.9, 8.3 Hz), 7.74 (1 H, d, J=8.3 Hz), 7.95 (1 H, d, J=1.9 Hz), 8.08 (1 H, s), 12.72 (1 H, br s)
1-016: MS (Pos, ES): 441 (M + 1)⁺, 443 (M + 3)⁺; NMR (200 MHz, CDCl₃) δ 1.10 (3 H, t, J=7.5 Hz), 1.85-2.38 (9 H, m), 2.84 (3 H, s), 3.42 (3 H, s), 3.89-4.10 (2 H, m), 5.38-5.51 (1 H, br s), 7.30-7.34 (3 H, m), 8.22 (1 H, s), 10.70-10.86 (1 H, br s)
1-018: MS (Pos, ES): 441 (M + 1)⁺, 443 (M + 3)⁺; NMR (300 MHz, CDCl₃) δ 1.10 (3 H, t, J=7.5 Hz), 1.90-2.35 (9 H, m), 2.84 (3 H, s), 3.42 (3 H, s), 3.90-4.08 (2 H, m), 5.40-5.50 (1 H, br s), 7.22-7.40 (3 H, m), 8.22 (1 H, s), 10.75-10.90 (1 H, br s)
1-020: MS (Pos, ES): 439 (M + 1)⁺, 441 (M + 3)⁺; NMR (300 MHz, CDCl₃) δ 1.01 (3 H, d, J=6.6 Hz), 1.09 (3H, d, J=6.6 Hz), 1.52-2.03 (6 H, m), 2.03-2.20 (7 H, m), 2.87 (3 H, s), 5.45-5.58 (1 H, m), 7.15 (1 H, s), 7.31 (2 H, s), 8.25 (1 H, s), 10.90-11.10 (1 H, m)
1-022: MS (Pos, ES): 457 (M + 1)⁺, 459 (M + 3)⁺; NMR (300 MHz, CDCl₃) δ 2.11(6 H, s), 2.85 (3H, s), 3.40 (6 H, s), 3.94-4.03 (2 H, m), 4.16-4.27 (2 H, m), 5.68 (1 H, br s), 7.28 (1 H, s), 7.32 (2 H, s), 8.20 (1 H, s)
*²HCl salt
*³ PhSO₃H salt Test Example [CRF Receptor Binding Test]

Monkey amygdala membranes were used as a receptor preparation.

¹²⁵I-CRF was used as ¹²⁵I-labeled ligand.

Binding reaction using the ¹²⁵I-labeled ligand was carried out by the following method described in The Journal of Neuroscience, 7, 88 (1987).

Preparation of Receptor Membranes:

Monkey amygdala was homogenized in 50 mM Tris-HCl buffer (pH 7.0) containing 10 mM MgCl₂, 2 mM EDTA and centrifuged at 48,000×g for 20 min, and the precipitate was washed once with Tris-HCl buffer. The washed precipitate was suspended in 50 mM Tris-HCl buffer (pH 7.0) containing 10 mM MgCl₂, 2 mM EDTA, 0.1% bovine serum albumin and 100 kallikrein units/ml aprotinin, to obtain a membrane preparation.

CRF Receptor Binding-Test:

The membrane preparation (0.3 mg protein/ml), ¹²⁵I-CRF (0.2 nM) and a test drug were reacted at 25° C. for 2 hours. After completion of the reaction, the reaction mixture was filtered by suction through a glass filter (GF/C) treated with 0.3% polyethylene imine, and the glass filter was washed three times with phosphate-buffered saline containing 0.01% Triton X-100. After the washing, the radioactivity of the filter paper was measured in a gamma counter.

The amount of ¹²⁵I-CRF bound when the reaction was carried out in the presence of 1 μM CRF was taken as the degree of nonspecific binding of ¹²⁵I-CRF, and the difference between the total degree of ¹²⁵I-CRF binding and the degree of nonspecific ¹²⁵I-CRF binding was taken as the degree of specific ¹²⁵I-CRF binding. An inhibition curve was obtained by reacting a definite concentration (0.2 nM) of ¹²⁵I-CRF with various concentrations of each test drug under the conditions described above. A concentration of the test drug at which binding of $^{125}$I-CRF is inhibited by 50% ($IC_{50}$) was determined from the inhibition curve.

As a result, it was found that compounds 1-001, 1-002, 1-003, 1-008, 1-009, 1-015, 1-017 and 1-021 can be exemplified as typical compounds having an $IC_{50}$ value of 100 nM or less.

Effect of the Invention

According to the present invention, compounds having a high affinity for CRF receptors have been provided. These compounds are effective against diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, irritable bowel syndrome, sleep disorders, dermatitides, schizophrenia, pain, etc.

What is claimed is:

1. A triaza-cyclopenta[cd]indene derivative represented by the following formula [I]:

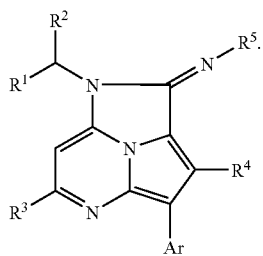

(wherein $R^1$ and $R^2$ are the same or different, and independently are hydrogen, $C_{1-6}$alkyl, $C_{3-7}$cycloalkyl, $C_{3-7}$cycloalkyl-$C_{1-6}$alkyl, $C_{1-6}$alkoxy-$C_{1-6}$alkyl, hydroxy-$C_{1-6}$alkyl, cyano-$C_{1-6}$alkyl, carbamoyl-$C_{1-6}$alkyl or di($C_{1-6}$alkyl)amino-$C_{1-6}$alkyl, cyano, carbamoyl or aryl;

$R^3$ is hydrogen, $C_{1-6}$alkyl, $C_{3-7}$cycloalkyl, $C_{3-7}$cycloalkyl-$C_{1-6}$alkyl, halogen, $C_{1-6}$alkoxy, $C_{3-7}$cycloalkyloxy, $C_{1-6}$alkylthio or —N($R^6$)$R^7$;

$R^4$ is hydrogen, $C_{1-6}$alkyl, $C_{3-7}$cycloalkyl or $C_{3-7}$cycloalkyl-$C_{1-6}$alkyl;

$R^5$ is hydrogen, $C_{1-6}$alkyl, aryl-$C_{1-6}$alkyl or carbamoyl;

Ar is aryl or heteroaryl which aryl or heteroaryl is unsubstituted or substituted with 1 or more substituents, which are the same or different, selected from the group consisting of halogen, $C_{1-6}$alkyl, $C_{3-7}$cycloalkyl, $C_{2-6}$alkenyl, $C_{2-6}$alkynyl, $C_{1-6}$alkoxy, $C_{1-6}$alkylthio, $C_{1-6}$alkylsulfinyl, $C_{1-6}$alkylsulfonyl, cyano, nitro, hydroxy, —$CO_2R^8$, —C(=O)$R^9$, —CONR$^{10}$R$^{11}$, —OC(=O)$R^{12}$, —NR$^{13}$CO$_2$R$^{14}$, —S(=O)$_r$NR$^{15}$R$^{16}$, trifluoromethyl, trifluoromethoxy, difluoromethoxy, fluoromethoxy and —N(R$^{17}$)R$^{18}$;

$R^8$ and $R^{14}$ are the same or different, and independently are hydrogen or $C_{1-5}$alkyl, $C_{3-8}$cycloalkyl, $C_{3-8}$cycloalkyl-$C_{1-5}$alkyl, aryl or aryl-$C_{1-5}$alkyl;

$R^6$, $R^7$, $R^9$, $R^{10}$, $R^{11}$, $R^{12}$, $R^{13}$, $R^{15}$, $R^{16}$, $R^{17}$, and $R^{18}$ are the same or different, and independently are hydrogen, $C_{1-6}$alkyl or $C_{3-7}$cycloalkyl;

r is 1 or 2;

or individual isomers thereof or racemic or non-racemic mixtures of isomers thereof, or pharmaceutically acceptable salts and hydrates thereof.

2. The triaza-cyclopenta[cd]indene derivative according to claim 1 represented by the formula [I], wherein $R^3$ is $C_{1-6}$alkyl; $R^4$ is hydrogen or $C_{1-6}$alkyl; $R^5$ is hydrogen or $C_{1-6}$alkyl; Ar is phenyl which phenyl is substituted with two or three substituents, which are the same or different, selected from the group consisting of halogen, $C_{1-3}$alkyl, $C_{1-3}$alkoxy, $C_{1-3}$alkylthio, trifluoromethyl, trifluoromethoxy and —N(R$^{17}$)R$^{18}$ (wherein R$^{17}$ and R$^{18}$ are the same or different, and independently are hydrogen or $C_{1-3}$alkyl); $R^1$, $R^2$ and $R^4$ are as defined in claim 1, or pharmaceutically acceptable salts and hydrates thereof.

3. The triaza-cyclopenta[cd]indene derivative according to claim 1 represented by the formula [I], wherein $R^3$ is $C_{1-3}$alkyl; $R^5$ is hydrogen or $C_{1-3}$alkyl; Ar is phenyl which phenyl is substituted with two or three substituents, which are the same or different, selected from the group consisting of halogen and $C_{1-3}$alkyl; $R^1$, $R^2$ and $R^4$ are as defined in claim 1, or pharmaceutically acceptable salts and hydrates thereof.

4. A composition, comprising a triaza-cyclopenta[cd]indene derivative, a pharmaceutically acceptable salt thereof or its hydrate according to claim 1, as an active ingredient and a pharmaceutically acceptable carrier.

5. A method for treating depression or anxiety comprising admnistering to a patient in need of treatment a pharmaceutically effective amount of the triaza-cyclopenta[cd]derivative, a pharmaceutically acceptable salt thereof or its hydrate according to claim 1.

* * * * *